US006521462B1

United States Patent
Tanouye et al.

(10) Patent No.: US 6,521,462 B1
(45) Date of Patent: Feb. 18, 2003

(54) DETECTING SEIZURE

(75) Inventors: Mark A. Tanouye, El Cerrito, CA (US); Daniel Kuebler, Kensington, CA (US); HaiGuang Zhang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/571,246

(22) Filed: May 16, 2000

(51) Int. Cl.[7] .............................. G01N 33/00; C12Q 1/00
(52) U.S. Cl. ..................... 436/149; 436/183; 436/806; 436/807; 435/4
(58) Field of Search .................... 436/149, 183, 436/806, 807; 435/4

(56) References Cited

PUBLICATIONS

Pavlidia et al., The Drosophila easily shocked Gene: A Mutation in a Phospholipid Synthetic Pathway Causes Seizure, Neuronal Failure, and Paralysis, Cell. (1994) 79:23–33.*

Pavlidis et al., "The Drosophila easily shocked Gene: A Mutation in a Phospholipid Synthetic Pathway Causes Seizure, Neuronal Failure, and Paralysis," Cell, vol. 79, Oct. 7, 1994, pp. 23–33.*

Pavlidis et al., "Seizures and Failures in the Giant Fiber pathway of Drosophila Bang–Sensitive paralytic Mutants," The Journal of Neuroscience, Aug. 1995, vol. 15, No. 8, pp. 5810–5819.*

Pruess et al., "Utility of the Mitochondrial Cytochrome Oxidase II Gene for Resolving Relationships among Black Flies (Diptera: Simuliidae)," Mol. Phylognet. Evol. (2000), 16(2), 286–295. (Abstract No.: 135:17070 CA).*

"Vinegar fly," britannica.com, Jun. 2001, one page.*

"Dipteran," britannica.com, Jun. 2001, 2 pages.*

* cited by examiner

Primary Examiner—B L Sisson
(74) Attorney, Agent, or Firm—Richard Aron Osman

(57) ABSTRACT

Methods and composition for inducing, detecting and modulating seizure in animal systems are provided. Methods for inducing seizure comprise (1) electrically stimulating an unanesthetized fly and detecting seizure induction in the fly (2) electrically stimulating a fly with less than 10V and detecting seizure induction in the fly; (3) electrically stimulating a population of wild-type flies and detecting seizure induction in most of the flies and (4) electrically stimulating a population of flies and quantitatively detecting seizure induction in the flies across genotypes or experience. Methods for modulating seizure induction comprise changing the activity of a novel seizure regulator in an animal system and confirming a resultant change in seizure inducibility of the system.

22 Claims, No Drawings

DETECTING SEIZURE

The research carried out in the subject application was supported in part by grants from the USPHS (Grant No. NS31231). The government may have rights in this invention.

INTRODUCTION

1. Field of the Invention

The field of the invention is inducing, detecting and modulating nervous system seizure in animal systems.

2. Background of the Invention

Human seizure disorders are a substantial health problem because of the large number of affected individuals and the variety of different syndromes. For example, an estimated 1% of the U.S. population is affected by over 40 different syndromes that make up the epilepsies (Hauser and Hesdorffer 1990; McNamara 1994; Commission 1989). All individuals are potentially vulnerable to seizures; they can occur in anyone following a sufficiently intense insult to the brain (Noebels 1996). Although seizures can occur in most anyone, individuals vary in what constitutes a seizure-inducing stimulus (Walton 1989; Sackheim et al. 1987). Some individuals have high seizure susceptibility such that they suffer spontaneous seizures while others have low susceptibility such that even head trauma or certain brain tumors would not lead to seizures (Walton 1989). Understanding what causes this variation in seizure susceptibility remains a fundamental problem in the study of human seizure disorders.

Relevant Literature

Aspects of this disclosure were published by Kuebler and Tanouye in J Neurophysiol. 2000 February;83(2):998–1009. Uchida (Nov 8, 1997, Biochim Biophys Acta, 1349, 13–24) reports the cloning of a mammalian ethanolamine kinase homolog of the eas gene product originally described by Pavlidis et al. (1994, Cell 79, 23–33).

SUMMARY OF THE INVENTION

The invention provides methods and composition for inducing, detecting and modulating seizure in animal systems. In a particular embodiment, the invention provides methods for inducing seizure in a fly, comprising the steps of (1) electrically stimulating an unanesthetized fly and detecting resultant seizure induction in the fly (2) electrically stimulating a fly with less than 20V and detecting resultant seizure induction in the fly; (3) electrically stimulating a population of wild-type flies and detecting resultant seizure induction in most of the flies and (4) electrically stimulating a population of flies and quantitatively detecting resultant seizure induction in the flies across genotypes or experience. In particular embodiments, the fly (or flies) is immobilized by mechanics, adhesive or vacuum, stimulated with an electrode tip having a diameter less than 20 um, and/or is a bang-sensitive mutant.

Exemplary subject methods for modulating seizure induction in an animal, comprise the steps of changing the activity of a seizure regulator in an animal system; and confirming a resultant change in seizure inducibility of the system, wherein the regulator is a seizure sensitive mutant suppressor or an enhancer not previously associated with seizure. In particular embodiments, the changing step alters the effective amount of the regulator in the system; the changing step comprises contacting the animal system with an effective amount of an anticonvulsive agent; and the animal system is a fly or a mouse.

A particular application of this method involves detecting agents which modulate seizure induction. In particular embodiments of this application, the changing step is preceded by the steps of (1) forming a mixture comprising a seizure regulator and an agent and detecting either binding of the agent to the novel regulator or a change in the binding of the regulator to a binding target; wherein the confirming step confirms that the agent modulates seizure induction in the system, or (2) forming a mixture comprising a gene encoding the novel regulator and an agent under conditions wherein but for the presence of the agent, the gene provides an unbiased expression and detecting an agent-biased expression of the gene, wherein a difference between the unbiased and agent-biased expression indicates that the agent modulates expression of the gene; wherein the confirming step confirms that the agent modulates seizure induction in the system.

DESCRIPTION OF SPECIFIC EMBODIMENTS OF THE INVENTION

The following descriptions of particular embodiments and examples are offered by way of illustration and not by way of limitation.

In particular embodiments, the invention provides methods for inducing seizure in a fly, comprising the steps of electrically stimulating a fly or population of flies and detecting resultant seizure induction. Any convenient method may be used to electrically stimulate the fly or flies, so long as it provides the requisite seizure induction. Generally, the stimulus is applied on an individual basis, wherein the fly is contacted with an electrode, particularly a relatively small tipped electrode having a tip diameter of less than about 50 um, preferably less than about 20 um, more preferably less than about 10 um, most preferably less than about 5 um, with lower limits bound only by construction and use constraints, generally being from between 0.1 and 1 um, see, e.g. Examples below.

The electrical stimulation required to induce seizure will depend on the fly and the manner in which the stimulation is delivered. With electrically sensitive flies, such as bang-sensitive mutants, seizure may be induced with a voltage of less than about 20V, preferably less than about 10V, more preferably less than about 5 V. With wild-type or suppressed mutants, the voltage requirement can range from 20 to 90V. Generally, at least about 0.1 to 1, and frequently from 1–4 volts are required even for the sensitive flies.

In a particular embodiment, the fly is unanesthetized, meaning that the fly is not subject to anesthesia nor post-anesthesia influences at the time of stimulation, as measured by a deviation from its normal quantitative parameters of seizure induction.

In a particular embodiment, the fly is immobilized to. facilitate direct stimulation. Immobilization may be effected by any convenient means, such as by mechanics, adhesive or vacuum.

Preferred methods provide for quantitative detection of seizure induction, particularly permitting the quantitative measurement of differences in parameters of seizure induction across genotypes and experience. Hence, seizure inducibility in examined animals can be compared to a quantitative scale of values of seizure inducibility, wherein the benchmarks are the quantitatively defined seizure-inducibilities of mutant and wild-type animals.

In particular embodiments, a population of flies is stimulated, generally by serially stimulating individual flies of the population. In one embodiment, the flies are wild-type flies and seizure is detected in a significant portion of the population, generally at least 10%, preferably at least 20%, more preferably at least 50%. In another embodiment, seizure is induced in the flies across genotypes or experience. A wide variety of experiences can be thus evaluated in terms of modulating seizure inducibility, including time, exposure to various stresses such as pharmaceutical agents, etc.

The invention provides a number of methods for modulating seizure induction in an animal. In a particular embodiment, the methods comprise the steps of changing the activity of a novel seizure regulator in an animal system and confirming a resultant change in seizure inducibility of the system. The novel regulator is an enhancer or suppressor of seizure induction, as measured by the assays disclosed herein, not previously associated with seizure. Novel suppressors include regulator is a suppressor gene, or expression product thereof, selected from the group consisting of Sh5, slo, netrin, eag, para, $Sh^{rko120}$, shak-$B^2$, $mle^{napts}$ and $Sh^{KS133}$. These genes and their products, including transcripts and translates, are well established in a variety of species; preferred homologs are Drosophila, mouse and human.

A wide variety of methods may be used to change the activity of the regulator, depending on the nature of the regulator and the animal. For example, the activity of voltage-gated $Na^+$ channels, such as $mle^{napts}$ and para, may be changed with an effective amount of a predetermined anticonvulsive agent, e.g. pharmaceutically active agents which specifically interact with such channels, such as phenytoin, carbamazepine and lamotrigine. In other embodiments, the regulator may be directly targeted with antibodies or intrabodies. Alternatively, the activity may be indirectly targeted, such as with competitive inhibitors such as dominant negative mutant forms of the regulator. In yet other embodiments, the expression of the regulator may be changed, for example by regulating the expression of the gene encoding the regulator or introducing vectors which increase (e.g. regulator expression constructs) or decrease (e.g. regulator antisense constructs) regulator expression. Similarly, any seizure inducible animal system may be used: widely used models are available for mouse, rat and fly (Drosophila) systems, see e.g. Seyfried TN, et al. (1999, Adv Neurol;79:279–90) for a review of experimental models of multifactorial epilepsies. the EL mouse and mice susceptible to audiogenic seizures.

A particular application of this method involves screening for and detecting agents which modulate seizure induction, encompassing in vitro, cell-based and animal-based screens. For example, the changing step may be preceded by forming a mixture comprising a novel seizure regulator and an agent, and detecting either binding of the agent to the regulator or a change in the binding of the regulator to a binding target; wherein the confirming step confirms that the agent modulates seizure induction in the subsequently employed animal system.

Alternatively, the changing step may be preceded by forming a mixture comprising a gene encoding the novel regulator and an agent under conditions wherein but for the presence of the agent, the gene provides an unbiased expression, and detecting an agent-biased expression of the gene, wherein a difference between the unbiased and agent-biased expression indicates that the agent modulates expression of the gene; wherein the confirming step confirms that the agent modulates seizure induction in the subsequently employed animal system.

EXAMPLES

I. Modifications of Seizure Susceptibility in Drosophila

Introduction: There are several advantages of studying seizure susceptibility in Drosophila. First; there is the availability of relevant mutants such as the Drosophila bang-sensitive (BS) paralytic mutants, which exhibit high susceptibility to seizures following mechanical and electrical shock (Pavlidis and Tanouye 1995; Ganetzky and Wu 1982). These mutants can be used in conjunction with the vast array of excitability and behavioral mutants in Drosophila to examine the types of molecular defects that can suppress or enhance seizure susceptibility. There are also excellent molecular genetic methodologies available for Drosophila, including P-element-mediated cloning methods as well as the rapidly expanding Drosophila genomic database. Finally, there is a variety of electrophysiological stimulation and recording methods available for the fly, including recordings from the adult giant fiber (GF) system that were used in this study (Tanouye and Wyman 1980; Trimarchi and Murphey 1997).

Although there are many advantages to using Drosophila as a model for human seizure disorders, any system that will be useful for studying seizure susceptibility must meet the following criteria. First, there must be a reliable way to test for seizure susceptibility across individuals and genotypes such that accurate seizure thresholds can be measured. Second, there must be an identifiable base-line level of seizure susceptibility in wild type strains such that relative comparisons can be made with mutants and experimentally altered individuals. Finally, seizures in the model system should exhibit similar characteristics with seizures in humans. In this study, we demonstrate that Drosophila meets these criteria and is in fact an attractive model for human seizure susceptibility defects. In addition, the data presented here also offer insights into the mechanisms that affect seizure susceptibility.

Materials and Methods: Fly stocks. *Drosophila melanogaster* strains were reared and studied at room temperature (22–24° C.). They were maintained on standard cornmeal agar medium. The BS mutants used in this study were easily shocked (eas), slamdance (sda) and bang-senseless (bss). The eas allele $eas^1$ was described previously (Pavlidis et al. 1994; Ganetzky and Wu 1982) and encodes an ethanolamine kinase involved in one pathway of phosphatidyl ethanolamine synthesis. The allele of bss used in this study, $bss^1$, was also previously described (Ganetzky and Wu 1982). The $sda^{iso7.8}$ allele is the most recent BS mutant identified and has been mapped to 97D (H. Zhang, personal communication). Wild type flies were either Canton-Special (CS) or Oregon (OR) strains. The maleless-no-action potential ($mle^{napts}$) mutant strain is a temperature-sensitive paralytic mutation affecting an RNA-helicase-like protein (Kernan et el. 1991; Lee and Hurwitz 1993) and is known to suppress bang-sensitive paralysis (Pavlidis and Tanouye 1995; Ganetzky and Wu 1982). The BS heterozygotes were generated by crossing the appropriate mutant with CS flies. We used predominately female flies in this study as their larger size made it easier to do electrophysiology.

Behavioral testing. Behavioral testing was performed on flies that were 2–3 days post-eclosion. Flies were allowed to rest two hours after exposure to anesthesia before testing. To test flies for the bang-sensitive phenotype, five flies were placed into a clean vial (Applied Scientific) and allowed to rest for 30 min. They were then vortexed on a VWR vortexer at maximum strength for 10 seconds. The flies were vortexed again 3–17 minutes later to determine if the flies were still refractory. Because of high variability in the behavioral refractory period, the refractory period values listed in the text are ranges of time spanning 2–5 minutes depending on the genotype. For each BS genotype tested, >85% of the flies had refractory periods that fell into the range listed.

Giant fiber electrophysiology. All flies used for electrophysiology were 2–3 days post-eclosion. The method used to stimulate and record giant fiber (GF) driven muscle potentials as well as to elicit seizures was as described (Tanouye and Wyman 1980; and Pavlidis and Tanouye 1995) with the following modifications. The fly was taken from a vial by attaching a 23 gauge needle to a vacuum hose and using this to suction onto the head of the fly. Once the fly was removed from the vial, another needle attached to a vacuum hose was used to suction to the abdomen thereby immobilizing the fly. In this way the fly could be affixed to a pin without anesthetizing the fly. In past studies (Pavlidis and Tanouye 1995), the flies were knocked out with ether prior to mounting, a technique that appears to reduce the excitability of the flies which in turn could artificially raise the voltage of the high-frequency (HF) stimulus necessary to elicit a seizure. In addition, we used tungsten stimulating electrodes, uninsulated tungsten wire (WPI 0.075 mm) electrolytically sharpened to a tip of a few microns, that were smaller and sharper than those used in previous studies. These electrodes cause less damage to the fly, thereby increasing the stability and reliability of the preparation.

Two types of stimulation were used, single-pulse stimulation and high-frequency stimulus wavetrains. Single-pulse stimuli (0.2 msec duration) delivered to the brain were used to drive the giant fiber (GF). In order to elicit seizures, HF stimuli (0.5 msec pulses delivered at 200 Hz for 300 msec) were delivered to the brain and the intensity (voltage) of the HF stimulus was varied as noted. Frequency of the stimulus also affected seizure susceptibility and was varied to 100 Hz and 50 Hz where noted. Using the techniques described above, the effective voltages for initiating seizures were much lower than recorded previously (Pavlidis and Tanouye 1995). In all protocols, the GF threshold for 0.2 msec single pulse stimulation was relatively constant, 1.5–3.0 V. For individual experiments in which the GF threshold was well above this range, the data were discarded. (Under the stimulation conditions employed here, the long latency pre-synaptic pathway seen by other investigators was observed less than 50% of the time (Engel and Wu 1996; Elkins and Ganetzky 1990). The recordings were all taken from muscle fibers, but we believe this to reflect accurately the activity of the motor neurons on a one-to-one basis for reasons described previously (Pavlidis and Tanouye 1995; Koenig and Ikeda 1983).

Determination of seizure thresholds and suppression thresholds. In order to determine seizure thresholds, HF stimuli were initially given to BS mutants at low intensities, 1–6 V depending on the genotype. If the stimulus was unsuccessful at eliciting a seizure, the intensity was subsequently increased in 1 V increments until a seizure was induced. The fly was allowed to rest five min between each HF stimulus. Once an initial seizure was induced, the fly was discarded. The seizure thresholds and seizure threshold curves presented represent a population of flies for that specific genotype. Thresholds were determined for individual flies as the lowest intensity at which seizures occurred. Individual thresholds were then compiled for each genotype to determine the mean threshold for that genotype. These threshold values are listed in Table 1. Seizure suppression thresholds were determined in much the same way and represent the mean voltage, above the seizure threshold, at which a particular genotype no longer undergoes seizure.

Because higher voltages were needed to determine suppression thresholds as well as seizure thresholds for wild type, eas/+, sda/+, and mle$^{napts}$ strains, in these cases, flies were never given more than two HF stimuli from which individual thresholds were determined. Thresholds for individual flies were then compiled as described for the BS mutants to determine mean thresholds.

Refractory period determination. Another set of experiments was conducted to investigate the electrical refractory period length. In these, an initial HF stimulus was delivered just above threshold to elicit a seizure. The HF stimulus intensities used were 7 V for sda, 4 V for eas and 3.5 V for bss. A subsequent HF stimulus of the same voltage was then given at varying time points following the initial seizure to determine if the fly, was still refractory. The end of the refractory period was determined as the time, rounded to the nearest 30 sec interval, at which 50% of the flies seized in response to the second HF stimulus. A similar protocol was used to determine seizure threshold changes for sda during the refractory period. In this case, the intensity of the second HF stimulus was varied from 6V, which is just below the seizure threshold, up to 100V. The second HF stimulus was delivered at various time points following the initial seizure. In this way, seizure thresholds were determined, as described previously, for each 60 sec time point during the sda refractory period.

Seizure length and latency changes. In order to analyze the difference between seizures elicited by HF stimuli with intensities near the seizure threshold and seizures elicited by HF stimuli with intensities near the suppression threshold, a single bss fly was given two seizures, one with a HF stimulus of 3–4 V and one with a HF stimulus of 12–15 V. The fly was allowed to rest 15 minutes between each HF stimulus. Half of the flies were given the 3–4 V buzz first while the other half were given the 12–15 V HF stimulus first. There was no obvious difference between the two protocols. The latency was measured as the time until the fifth spike following the HF stimulus. This was done to control for random spikes that occasionally appeared after the HF stimulus but before the seizure. The length of the seizure was measured as the time from the fifth spike to the cessation of spiking activity in the muscle.

Thoracic ganglia stimulation. To stimulate the thoracic ganglia, flies were mounted on a pin in the same manner as described above. The stimulating electrodes were bent at 45 degree angles and inserted just through the anterior preepisternum (near the base of the first coxa) with the help of a mirror placed at an angle under the fly. Following single-pulse (0.2 msec) stimulation, usually two DLM responses could be seen as described previously (Salkoff and Kelly 1976), a short latency response, stimulation of the DLM motor neuron directly, and a long latency response. Seizures where induced with a standard 300 msec HF stimulation of 0.5 msec pulses at 100 Hz. Seizure thresholds for thoracic stimulation were calculated as described previously. Thresholds were more variable in the thorax, most likely due to the higher variability. of electrode placement in this preparation compared with brain stimulation.

Recordings in Haemolymph Solution

When recording from the TTM, some experiments were done with the thorax under saline to be sure that the TTM seizure activity was not pick-up from other neighboring muscles. We found that the TTM activity was not pick-up from other muscles as no differences were seen between TTM seizure activity under saline and that seen under normal conditions. In order to record under saline, flies were suctioned as previously described and then the wings and legs were removed with dissecting scissors. The fly was then embedded in wax in a petri dish above a polyethylene tube with a hole cut in it to supply air to the fly. Wax was pressed up against the thoracic cuticle and the abdomen was covered. Wax was then placed over the thoracic connective such that the head and thorax were separated by a wax barrier. Haemolymph-like solution, HL3, (Stewart et al. 1994) was allowed to cover the thorax while the head was exposed to the air. Insulated tungsten recording electrodes (WPI) were placed into DLM, DVM and TTM muscles and a ground electrode was placed in the bath. The stimulating electrodes were the same as described previously.

Recordings from leg and direct flight muscles. In order to record from both leg and direct flight muscles, flies were mounted to pins as described above. The tibia levator muscle (TLM) recordings from the mesothoracic leg were done as previously described (Trimarchi and Schneiderman 1993) except that glue was used in place of wax to affix the leg. Intercoxal lateral levator muscle (ILLM) recordings from the prothoracic leg were prepared in a similar fashion and then recording electrodes were inserted dorsally along the long axis of the coxa. In recordings of direct flight muscles, the thorax was tilted approximately 90° relative to the head to allow insertion of the recording electrodes into the direct flight muscles based on external cuticle markers (Heide and Gotz 1996; Tanouye and King 1983). The direct flight muscles recorded from here, the anterior pleural muscle 1 (PA1) and the anterior pleural muscle 3 (PA3) (King and Tanouye 1983), were identified by both external markers and stimulation threshold. When recording from direct flight muscles, simultaneous recordings were made in underlying DVM muscles to determine if the activity seen in the direct flight muscles was pick up from the larger DVM's. The activity was never synchronous.

Results: The features of BS mutant seizures described here are similar to those reported previously (Pavlidis et al. 1994; Pavlidis and Tanouye 1995). A short intense train of electrical stimuli delivered to the brain causes seizure-like activity, which is observed as abnormal high-frequency (~100 Hz) firing of the DLM motoneurons lasting 1–2 sec. The "seizure" is followed by failure of the giant fiber (GF) pathway for a period of time that varies depending upon the genotype. The present study shows significant differences in our ability to define seizure susceptibility and the ways in which it may be modulated. This comes about, in large part, from eliminating anesthesia and using smaller diameter tungsten electrodes, both of which appear to keep brain neurons substantially healthier. For example, activation thresholds for the giant fiber (GF) neuron in this study are in the 2–3 V range (down from ~10 V; Tanouye and Wyman 1980; Pavlidis et al. 1994; Pavlidis and Tanouye 1995). Also, seizures are evoked at much lower voltages. For example, in bss mutants, the seizure threshold is 3.1 V (down from 50 V in Pavlidis and Tanouye 1995). The resolution, reproducibility, and reliability of results allow us, for the first time, to quantify features of seizure initiation in Drosophila and to ascertain how these features vary across genotypes and with past experience.

Seizure Susceptibility Varies with Genotype

In previous studies (Pavlidis and Tanouye 1995), seizures were evoked in BS mutants and were almost never seen in wild type flies even at the highest voltage tested, 100V. In the present experiments, seizures are evoked consistently in CS wild type flies at a threshold of 44.5±4.4 V (Table 1). Seizures in CS flies were qualitatively similar to BS seizures in terms of the spiking activity observed in the DLM and were followed by the usual period of synaptic failure although the frequency of the spontaneous seizures during recovery was reduced significantly. In addition, the synaptic failure period was shorter in CS flies, 40±12 sec (n=14), than the values previously obtained for different BS mutants which range from 46±20 secs to 112±70 secs (Pavlidis and Tanouye 1995). A second wild type strain, OR was used to verify the ability of wild type flies to undergo seizure and was found to be similar in phenotype to CS indicating that the overall response to high intensity stimuli is similar for both BS mutants and wild type flies. For OR, the threshold for seizure is 48.4±3.6 V. Not surprisingly, there does appear to be some variation in seizure threshold for different wild type strains, however, this variation is quite small when compared to the effects of the different genetic mutants discussed below.

The major difference between wild type and all BS mutant flies is that the latter seize at far lower HF stimulus intensities. For example, in bss, the most susceptible of the BS mutants, seizures occur at only 3.1±0.7 V, or about 13-fold lower than that seen for CS (Table 1). Each of the BS mutants studied has a characteristic HF stimulus intensity for eliciting seizures, the seizure threshold, that is much lower than wild type; 3.6±0.7 V for eas and 6.8±1.0 V for sda. These mutants demonstrate that seizure susceptibility can be enhanced by genetic mutation. We have also found that the seizure susceptibility can be suppressed in certain mutants. The hypoexcitability mutant $mle^{napts}$ has a much higher characteristic threshold than wild type. In fact, even at the highest voltages tested, 100V, seizures only occurred in 11% of these flies (n=18). These data demonstrate that seizure thresholds can be modulated by genetic mutations over a large range in Drosophila.

Individual neuron excitability is similar in normal and mutant flies. A possible explanation for genotypic differences in seizure susceptibility is that each individual neuron in BS mutants could be hyperexcitable. In this case, a low intensity HF stimulus in the BS mutants could be directly activating the same number of neurons as a high intensity HF stimulus in wild type. There is some precedent for thinking that this might occur since one source of seizure disorder in mice corresponds with the knockout of a voltage-gated $K^{30}$ channel, which would presumably cause membrane hyperexcitability (Smart et al. 1998). Experiments examining GF excitability indicate that this is not an explanation for the Drosophila BS mutant phenotype as the stimulus voltages required for activation of the GF did not differ among genotypes (Table 1). For example, the GF activation threshold for CS (2.4±0.44 V) is virtually identical to that of bss (2.3±0.42 V). GF activation thresholds for other genotypes are also in the same range (Table 1) with the exception of $mle^{napts}$ (3.1±0.24) which has a slightly elevated GF threshold. We also tested another group of neurons, the DLM motoneurons, to further examine the excitability of individual neurons. The thresholds for DLM motoneuron activation are 1.52±0.37V for $mle^{napts}$, 1.31±0.24V for bss and 1.35±0.33 V for CS, a further indication that alterations in individual neuron excitability does not account for the large differences in seizure susceptibility seen between BS mutant and wild type.

For bss, the GF activation voltage and the voltage for evoking seizures are very close to each other and their variability nearly overlaps. However, when examined on a case by case basis, the GF activation voltage was lower. Since at its threshold, the GF appears to be the only neuron activated, we interpret this to mean that, despite its extensive motor outputs, stimulation of the GF alone is not sufficient to evoke a seizure. Even. in the case of bss, the most susceptible. of our mutants, the HF stimulus is recruiting other higher threshold (i.e. smaller diameter) neurons, some of which have been described previously (Tanouye and Wyman 1980; Tanouye and King 1983), and recruitment of these other neurons is necessary to trigger seizures. The fact that low voltages are required in bss flies indicates that relatively few of these other neurons need to be recruited by the HF stimulus to initiate seizures. Higher voltages are required for wild type flies indicating that many more neurons must be recruited for seizure initiation in these flies. Thus, our date indicate that the increased seizure susceptibility seen in BS mutants corresponds to a reduction in the minimum number of neurons that must be recruited by a HF stimulus in order for a seizure to initiate.

Altering the frequency of pulses within a HF stimulus affects seizure susceptibility. The foregoing data indicate that single cell excitability does not play a substantial role in defining the range of seizure susceptibility in normal and mutant Drosophila. Rather, for each genotype, we conclude there is a characteristic minimum number of brain neurons that must be driven synchronously by the pulses within a HF stimulus. For some mutants, such as bss this minimum is a very small number of neurons; for wild type a much larger number of neurons must be driven. Furthermore, by altering the HF stimuli in characteristic ways, we are able to modify seizure susceptibility in a fashion consistent with the notion that we are redefining the minimum number of neurons that must be driven.

One very interesting way in which seizure thresholds may be modulated is by varying the frequency within the HF stimulus. An example of the effect of frequency on seizure initiation can be seen in bss flies. In this case, the seizure threshold for frequencies of 200 Hz, 100 Hz, and 50 Hz increases from 3.1±0.7 to 5.1±1.2 to 6.8±1.1 V, respectively. Varying the frequency had comparable effects for sda and eas mutants. It appears that the individual pulses present in the HF stimulus are somehow integrated by the neurons that are responsible for generating the seizure; there is some form of temporal summation taking place. If the number of neurons recruited by a 4V HF stimulus is always the same, the frequency is expected mainly to affect the firing rate of these neurons. At higher frequencies, the increased rate of firing is temporally summated by the underlying excitatory circuits and a seizure results. At lower frequencies, temporal summation is not as effective, therefore a larger number of neurons must be driven in order to initiate seizure.

Seizure thresholds in heterozygote flies. The three BS mutants described here are similar in several respects. They have similar behavioral phenotypes; as well as seizure and synaptic failure phenotypes. They are not, however, identical, and one of the most salient differences emerges in heterozygous flies. The situation for each of the mutations, bss, eas, and sda, is completely different as heterozygotes (Table 1). The eas mutation acts as a recessive when examined electrophysiologically. Seizures are evoked in eas/+ flies at a HF stimulus intensity of 43.2±3.8 V., very close to the wild type value. This is qualitatively similar to the behavioral phenotype of eas which is completely recessive (Ganetzky and Wu 1982). In contrast, bss acts almost as a completely dominant mutation. Seizures are evoked in bss/+ flies at a HF stimulus intensity of 6.7±1.1 V., close to the value of bss homozygotes. This also is consistent with what is seen behaviorally (Ganetzky and Wu 1982). The sda mutation, however, has quite an interesting phenotype. It acts as a semi-dominant mutation in the seizure assay, while behaviorally it acts as a recessive. Seizures are evoked in sda/+ flies at a HF stimulus intensity of 30.6±4.5 V., in between the values for mutant homozygotes and wild type, although somewhat closer to wild type.

Taken together, we have examined a total of nine different genotypes. For each genotype, seizures are elicited by a HF stimulus with a characteristic voltage allowing us to use this as a measure for defining seizure susceptibility. In this way, susceptibility is found to vary over a considerable range, from 3V to 100V. Genotypes that display a high susceptibility to seizures (i.e. low seizure threshold value: bss, eas, sda, bss/+) also have a strong bang sensitive behavioral phenotype and genotypes that display a lower susceptibility to seizure (i. e. higher seizure threshold value: sda/+, eas/+, CS, OR, mle$^{napts}$) are not bang sensitive. Having a characteristic seizure threshold for a particular genotype now allows us to examine changes in seizure susceptibility over time.

Seizure thresholds shift during the refractory period. Behavioral bang sensitivity varies according to genotype; it can also vary according to previous experience. Upon recovery from paralysis, BS mutants cannot be re-paralyzed by a second bang stimulus for a period of time that varies according to genotype (Grigliatti et al. 1973; Judd et al. 1972; Ganetzky and Wu 1982). This is termed the refractory period. For bss, eas, and sda, the refractory period is 10–15 min, 8–10 min, and 5–7 min, respectively. If the behavioral bang sensitivity is correlated with seizure susceptibility, we reasoned that following a seizure, there might be an increase in the HF stimulus intensity required to elicit a second seizure. That is, the refractory period might be the result of a transient change in seizure susceptibility resulting from a previous bout of seizure. In order to determine this, sda flies were given an initial seizure at threshold, 7 V. At 60 sec intervals following the initial seizure, HF stimuli of various intensities were applied to determine susceptibility to a second seizure. One minute after the initial seizure, the threshold for a second seizure is very high, 94±6.4 V. This indicates that there is a large decrease in seizure susceptibility immediately following an initial seizure. In this case, the 94 V threshold indicates that sda is much less susceptible to seizure than wild type flies. The change in seizure susceptibility is transient; as the time following the first seizure increases, the threshold continuously falls. At 2 min, sda has about the same susceptibility as wild type flies, 55±8.6 V, while at 5 to 6 min, the seizure threshold has fallen to near the initial seizure threshold for sda. Thus, even within a single genotype seizure susceptibility is quite plastic. Immediately following an initial seizure, susceptibility is modulated by some process that causes a large threshold increase. Seizures may still be elicited at this time, however, a HF stimulus of higher intensity must be used. This is presumably because a much greater number of neurons must be stimulated. Whatever this process is, it appears not to involve an increase in individual nerve cell excitability as there is no change in GF threshold during the refractory period.

For sda, the changes in seizure susceptibility following an initial seizure resemble what is expected for an explanation of the behavioral refractory period. In the case of sda, the duration of the susceptibility change is similar to the duration of the behavioral refractory period, and during most of this time, sda is not very susceptible to seizures, the threshold is in the range of wild type. There are also seizure susceptibility changes in bss and eas following an initial seizure. These changes are generally similar to those seen for sda, however, they provide an incomplete explanation for bss and eas behavioral refractory periods. The duration of the susceptibility change in both of these mutants is not as long as the behavioral refractory period. For bss, the seizure susceptibility change lasts 6 min while the behavioral refractory period is 10–15 min. Similarly, the duration of the seizure susceptibility change in eas is 4 min; also shorter than the behavioral refractory period, 8–10 min. In addition, the change in the seizure threshold is not very great. At 60 sec following the initial seizure, a second seizure may be elicited by ~8 V HF stimuli for bss and ~10 V HF stimuli for eas. These HF stimulus intensities are substantially less than that seen for wild type and it seems as if these mutants should still be bang sensitive. Taken together, these results indicate that changes in seizure susceptibility can contribute to the behavioral refractory period.

This change in susceptibility following a seizure is not limited to the BS mutants but occurs in wild type strains as well. One minute following an initial seizure, CS flies are highly resistant to seizure as a 100 V HF stimulus only triggered a seizure in one out of nine flies tested. Thus, these flies were much less susceptible to seizure than they had been initially.

Seizures are not seen at high stimulus intensities. The characteristic HF stimuli that elicit seizures for a given genotype behave in an all-or-nothing manner. That is, below threshold, seizures are never elicited, while just above threshold, seizures are elicited and spread throughout all muscle groups examined (see below). However, if HF stimulus intensities are increased well above threshold, there are changes in the form of the seizure. These changes consist of the latency to seizure becoming shorter and less variable and the seizure becoming shorter in duration. For example, in bss a 4 V HF stimulus elicits a seizure with a 410±95 msec latency and 730±120 msec duration while a 12 V HF stimulus elicits a seizure with a 190±65 msec latency and 460±155 msec duration.

As HF stimulus intensity is increased further, a surprising thing occurs that we have termed "high voltage seizure suppression". We have found, in certain genotypes, that high stimulus intensities are not effective at eliciting seizures. For example, in bss, we occasionally observe seizure suppression following HF stimuli of 10 V. As HF stimulus intensity is increased from 10 V to 20 V, fewer HF stimuli are effective in eliciting seizures. For HF stimuli greater than 20 V, seizures are never observed in bss. High voltage seizure suppression in bss has a threshold of 12.5±3.4 V. This observation describes a very curious situation for bss: there is only a small window of HF stimulus intensities, between about 3 and 12 V, that are effective in eliciting seizures.

High voltage seizure suppression is also observed in eas, sda, and bss/+ flies. For each genotype that shows suppression, there is a characteristic voltage, the suppression threshold, at which it occurs: bss (12.5±3.4V)~eas (10±2.9V)<<sda (63±8.0 V)~bss/+(59±7.1 V). There appears to be a relationship between the seizure threshold value and the suppression threshold value. The rank order of genotypes from the lowest to the highest is roughly the same, with suppression thresholds about 4 to 9 times higher than seizure thresholds for these genotypes. This suggests that technical limitations are responsible for the genotypes that do not show suppression here; sda/+, eas/+, CS, OR and mle$^{napts}$. Extrapolating from their seizure thresholds, these genotypes would all have predicted suppression thresholds of greater than 100 V, too large to be sampled in these experiments.

In order to investigate the physiological cause of suppression in bss flies, we examined how the GF circuit functions immediately following the HF stimulus. Following low intensity HF stimuli (4–12V), the GF circuit is functional from the end of the HF stimulus to the onset of seizure. That is, single-pulses are effective in activating the GF as muscle potentials are evoked in the DLMs via the circuit. Following high intensity HF stimuli (~20V) that lead to suppression of seizure, we find that the GF pathway is not functional. From the earliest times we can measure following a 20V HF stimulus in these flies (about 10 msec), the GF circuit does not support DLM evoked potentials. We cannot be certain that at the early time points following the HF stimulus whether it is synaptic failure, the activation of inhibitory inputs or some other process that limits GF circuit operation, however, it is known that at later time points it is synaptic failure (Pavlidis and Tanouye 1995). It is clear though that increasing the voltage of the HF stimulus decreases the latency to failure of the GF pathway in much the same way that increasing the voltage of HF stimulus causes the latency to seizures to decrease in bss flies (see above).

Seizure suppression interferes with the spread of seizures. When the HF stimulus voltage delivered to the fly is at the seizure or suppression threshold, the results are generally similar. Some HF stimuli are effective and widespread seizures are elicited; some HF stimuli are not effective and do not elicit seizure. In fact, this is always the case for HF stimuli at the seizure threshold. However, at suppression threshold, a third type of response is occasionally (<10% of stimuli) observed: seizures are observed in some muscles, but not others. Recordings from two ipsilateral DLM fibers show that in every case, the motoneurons innervating these fibers either both seize or both show suppression. In contrast, if the same HF stimulus is applied and two contralateral DLM fibers are examined, occasionally one DLM motoneuron would seize, but not the other. We infer that these are cases of partial or incomplete seizure suppression such that the seizure can spread to an ipsilateral, but not to a contralateral DLM. In the case of partial suppression, we know that by using a slightly higher HF stimulus voltage, we can further suppress the spread of seizure such that it is not seen in any of the DLM motoneurons.

Thoracic ganglion stimulation. The validity of our findings on BS mutants can be tested by delivering HF stimuli to the thoracic ganglion. Ganglion stimulation is also effective at eliciting seizures and can help distinguish variation due to electrode position, to damage due to electrode placement and to other aspects specific to the brain. In general, the basic features of seizure susceptibility and modification are conserved in the two preparations, although there are some quantitative differences. HF stimuli delivered to the thoracic ganglia of CS, bss and mle$^{napts}$ flies elicit seizures and synaptic failure. The seizures are generally similar to those described previously, although there are quantitative differences in the latency and duration of the seizures, probably due to seizures reaching the DLMs by different pathways than for brain stimulation. For bss mutants, ganglion HF stimulus intensities that are effective for eliciting seizures are lower than those for wild type indicating again that the BS mutants are more susceptible to seizures. Using 100 Hz HF stimuli, these three genotypes have seizure thresholds of 3.3±0.56 V for bss, 9.5±2.9 V CS and 23±4.8 V for mle$^{napts}$. As only 100 Hz HF stimuli were used for thoracic ganglion stimulation, the intensity of the ganglion HF stimulation required to elicit seizure is lower than that seen in brain HF stimulation for all genotypes tested.

The extent of seizures. DLM muscle potentials provide a convenient way to monitor how genotype and experience contribute to seizure susceptibility. In addition, the GF system, particularly the GF to DLM pathway provides a convenient way to test for neural circuit properties such as synaptic failure. However, we find that seizures spread throughout a much larger population of thoracic motoneurons. The spread is to all motoneurons that we have recorded from including both GF system and non-GF system outputs. In the GF system, we have observed seizure spread to all known outputs: TTM, DLM, DVM, PA1 and the mesothoracic leg TLM muscles. We have also observed seizure spread in non-GF system outputs including PA3 and prothoracic leg ILLM muscles. Thus, seizures spread extensively throughout the thoracic ganglion motoneuron population; it could be that the entire population is involved.

Since seizures are known to spread through the nervous system along particular pathways (Noebels 1996), we reasoned that we might see latency differences in seizure onset in the various motoneurons. Seizure might spread to some motoneurons by a rather direct route, while spread to others may occur via a less direct route. In fact, our data show that the latency to seizure onset in a DLM and a TTM muscle in the same bss fly were not identical. The latency to seizure onset in the DLM is 450 msec, while the latency in the TTM is 700 msec. This result is repeatable as seizure activity is not seen in the TTMs until 303±48 msec (n=12) after seizures begin in the DLMs when bss. flies are given HF stimuli near the seizure threshold. These latencies do not appear to be greatly affected by genotype as roughly similar values are observed for eas, seizure activity in TTMs was delayed 215±75 msec (n=8) compared to DLMs. This result is opposite to that seen following single pulse stimulation of the GF pathway where the DLM response has a longer latency than the TTM response (Tanouye and Wyman 1980). This indicates that different pathways to these muscles must exist and can be recruited differentially by different stimulus regimes. Seizures spread to other motoneurons with characteristic latencies. For example, DLMs, DVMs and ILLMs have a short latency and display seizure activity on the same time scale, while TTMs and TLMs have a longer latency.

Although the pathways for seizure spread are not known, there may be ways to dissect them. As described earlier, during high voltage seizure suppression, seizures are sometimes seen in the ipsilateral, but not the contralateral DLMs. This suggests that seizures spread to these two muscles by different pathways. We infer that the point of divergence must be above the level of the DLM motoneurons because all of the motoneurons innervating the different fibers of the same muscle always behave similarly and because suppression always occurs in an all-or-nothing manner.

Genetic and Experience-Dependent Modifications of Seizure Thresholds. Previous studies of seizures in Drosophila found that certain mutants, the BS mutants, undergo seizure in response to electrical shock (Pavlidis and Tanouye 1995). Due to experimental limitations in that study (supra), seizures were rarely seen in other genotypes. Here, we have been able to demonstrate that each genotype, whether wild type or mutant, has a characteristic or signature HF stimulus intensity at which seizures occur. This is the first demonstration that wild type flies consistently undergo seizure following electrical shock, however, it should not be surprising as it appears that all higher nervous systems have the capacity for seizure following high-intensity stimuli (Noebels 1996). For example, human subjects have seizures in response to electro-convulsive therapy (ECT), while repeated high intensity stimuli can lead to the kindling of seizures in many animals and brain tissue preparations (Loscher 1997; Fisher 1989). The defect then in the BS mutants is not that they have seizures, but rather that the mutation modifies the seizure threshold, in this case making the flies more susceptible to having seizures than wild type strains. Genetic mutations can also make flies less susceptible to having seizures as in the case of mle$^{napts}$. In fact, we have found that seizure thresholds can be modified genetically over a very wide range, from 3V to above 100V, in this study.

An interesting example of the genetic modification of seizure thresholds is found in looking at heterozygous flies. Unlike the BS mutants whose thresholds fall in a narrow range, 4V, the heterozygote thresholds vary over a range of 35 V. These differences cannot always be predicted by their behavior, particularly in the case of sda/+. These flies show how a single copy of the sda mutation can lead to a significant difference in seizure susceptibility compared to wild type, 14V, even though the behavior is normal. This may be due in part to different pathways being responsible for the behavioral and electrophysiological phenotypes. The sda/+ result indicates that mutations that appear behaviorally inconsequential, can alter seizure thresholds in perceptible ways. This is also seen in humans in some forms of idiopathic epilepsy (Walton 1989) and in certain mice knockouts (Signorini et al. 1997; Erickson et al. 1996). In addition to genetic mutations, the previous experience of the fly also modifies seizure susceptibility. Immediately following a seizure-inducing HF stimulus there is an abrupt jump in the seizure threshold, which does not coincide with any noticeable change in the threshold of individual neurons. The increase in threshold following a seizure is a well-established phenomenon in mammals. In humans the seizure threshold can remain elevated for a few days (Sackeim et al. 1983; Sackeim et al. 1987) while in rats in can remain elevated for a few hours (Green et al. 1982). Since both wild type and mutant flies exhibit threshold increases following a seizure, it appears to be a normal response to seizure in Drosophila as well.

There are many reasons Drosophila offers an attractive model for understanding seizure susceptibility in humans. For example, one BS mutant, tko, has been linked with the gene product involved in human myoclonic epilepsy/ragged red fiber (MERRF) disease, as they both encode proteins involved in mitochondrial protein synthesis (Royden et al. 1987; Shoffner et al. 1990). In addition, both the BS defect and the seizure disorders associated with epilepsy are conditional defects in that seizures occur interspersed within periods of normal nervous system function often during which no obvious behavioral or neuronal defects can be detected. The data presented here gives a much more detailed understanding of seizures in Drosophila and demonstrates that they are similar to seizures seen in humans. The thresholds for seizure activation in Drosophila can be affected by genetic mutations such as the BS mutants or mle$^{napts}$, just as the threshold in humans and mice can be modified by genetic mutations that lead to epilepsy. In addition, electrically induced seizures in Drosophila cause a transient increase in the seizure threshold, similar to what is seen in rats and humans. The seizures can be monitored throughout the nervous system and they spread in a defined manner through the fly. This again is consistent with many mammalian seizure disorders. These and previous findings indicate that similar mechanisms underlie changes in seizure susceptibility in both flies and humans. These similarities, coupled with the ability to accurately quantify the seizure threshold across genotypes and over time, give us a powerful system in which to investigate the types of molecular defects that make the nervous system most vunerable to seizures.

REFERENCES

Commission on Classification and Terminology of the International League Against Epilepsy, *Epilepsia* 30:389–399, 1989.

Elkins, T. and Ganetzky, B. *J. Neurogenetics* 6(4):207–219, 1990.

Engel, J. E. and Wu, C. F. *J Neurosci.* 16(10):3486–3499, 1996.

Erickson, J. C., Clegg, K. E., and Palmiter, R. D. *Nature* 381:415–418, 1996.

Ganetzky; B. and Wu, C. F. *Genetics* 100:597–614, 1982.

Green, A. R. et al. Sandler, M (ed) Oxford University Press, Oxford, 1982.

Grigliatti, T. A. et al. *Molec. Gen. Genet.* 120: 107–114, 1973.

Hauser, W. A. and Hesdorffer, D. C. New York: Demos, 1990.

Heide, G. and Gotz, K. G. *J. Exp. Biol.* 199:1711–1726, 1996.

Judd, B. H. et al. *Genetics* 71: 139–156, 1972.

Kernan, M. J. et al. *Cell* 66(5):949–959, 1991.

King, D. G. and Tanouye, M. A. *J. Exp. Biol.* 105:231–239, 1983.

Koenig, J. H. and Ikeda, K. *J. Comp. Physiol.* 150:295–303, 1983.

Lee, C. G. and Hurwitz, J. *J. Biol. Chem.* 268(22):16822–16830, 1993.

Loscher, W. *Prog. in Neurobiol.* 53(2):239–258, 1997.

McNamara, J. O. *J. Neurosci.* 14(6):3413–3425, 1994.

Noebels, J. L. *Neuron* 16(2):241–244, 1996.

Pavlidis, P. et al. *Cell* 79(1):23–33, 1994.

Pavlidis, P. et al. *J. Neurosci.* 15(8):5810–5819, 1995.

Royden, C. S. et al. *Cell* 51:165–173, 1987.

Sackeim, H. A. et al. *Biol. Psych.* 18(11):1301–1310, 1983.

Sackeim, H. A. et al. *Arch. Gen. Psych.* 44(4):355–360, 1987.

Salkoff, L. and Kelly, L. *Nature* 273:156–158, 1976.

Shoffner, J. M. et al. *Cell* 61: 931–937, 1990.

Signorini, S. et al. *Proc. Natl. Acad. Sci. USA* 94:923–927, 1997.

Smart, S. L. et al. *Neuron* 20:809–819, 1998.

Stewart, B. A. et al. *J. Comp. Physiol.* A 175:179–191, 1994.

Tanouye, M. A. and King, D. J. *J. Exp. Biol.* 105: 241–251, 1983.

Tanouye, M. A. and Wyman, R. J. *J. Neurophysiol.* 44:405–421, 1980.

Trimarchi, J. R. and Murphey, R. K. *J. Neurosci.* 17(12):4700–4710, 1997.

Trimarchi, J. R. and Schneiderman, A. M. *J. Exp. Biol.* 177:149–167, 1993.

Walton, L. Essentials of Neurology. 6th ed Churchill Livingstone Pub, 77–86, 1989.

TABLE 1

Threshold values for the various strains tested.

| Strain | Giant Fiber Threshold | Seizure Threshold | Suppression Threshold |
|---|---|---|---|
| bss | 2.3 ± 0.42 | 3.1 ± 0.7 | 12.5 ± 3.4 |
| eas | 2.3 ± 0.40 | 3.6 ± 0.7 | 10.3 ± 2.9 |
| sda | 2.2 ± 0.38 | 6.8 ± 1.0 | 63 ± 8.0 |
| bss/+ | 2.4 ± 0.31 | 6.7 ± 1.1 | 59 ± 7.1 |
| sda/+ | 2.3 ± 0.29 | 30.6 ± 4.5 | — |
| eas/+ | 2.5 ± 0.29 | 43.2 ± 3.8 | — |
| CS | 2.4 ± 0.44 | 44.5 ± 4.4 | — |
| OR | 2.4 ± 0.41 | 48.4 ± 3.6 | — |
| mle$^{napts}$ | 3.1 ± 0.24 | >100 | — |

Values for the GF threshold, seizure threshold and the suppression threshold (if any) are listed for each genotype that was tested. The four genotypes listed in bold type are sensitive to mechanical shock while the others are resistant.

CS, OR, sda/+, eas/+ and mle$^{napts}$ strains showed no seizure suppression even at the highest voltage tested, 100V. (n>13 for each genotype tested.)

II. Genetic Suppression of Seizure Susceptibility in Drosophila

Seizure susceptibility is largely influenced by genetic factors. At present, more than a dozen genes have been linked to various epilepsy syndromes in humans, while in mice more than genetically mutated strains have epileptic phenotypes (McNamara, 1999; Puranam and McNamara, 1999). Genetic factors can also suppress seizures and epileptogenesis. Mice with mutations in the brain-derived neurotrophic factor gene (BDNF) or the immediate early gene c-fos both display delayed onset of seizures following kindling (Kokaia et al., 1995; Watanabe et al., 1996). In addition, the variable penetrance of human epilepsy genes (Durner et al., 1991; Biervert et al., 1998) indicates that other genetic factors can, in certain cases, suppress the development of spontaneous seizures.

One group of mutants that exhibit increased seizure susceptibility is the bang-sensitive (BS) mutants (Benzer, 1971; Ganetzky and Wu, 1982; Pavlidis and Tanouye, 1995) which are 5–10 times more susceptible to seizure following electrical shock than wild type flies (Kuebler and Tanouye, 2000). BS mutants can be used to assay the types of genetic changes that can rescue seizure susceptible phenotypes. It is clear that genetic factors can suppress seizures in BS mutants as stocks require continuous selection to maintain a robust BS phenotype. The identification of these factors can be accomplished by assaying the ability of other well characterized mutants to suppress the BS phenotype.

Materials and Methods. Fly stocks. Wild type Drosophila strains were Canton Special (CS), Oregon-R (OR) and Berlin. The easily shocked gene (eas) is located at map position 1-53.5 and encodes an ethanolamine kinase (Pavlidis et al., 1994). The bang senseless gene (bss) is located at 1-54.6 and slamdance (sda) on the third chromosome at 97D8-9 (Ganetzky and Wu, 1982; H. Zhang, unpublished observations); their gene products have not been described. The mutant behavioral phenotypes of seizure and paralysis, electrophysiological phenotypes of seizure and synaptic failure, and the threshold for seizure susceptibility have been described previously for the bss$^1$, eas$^1$, and sda$^{iso6.10}$ mutations (Ganetzky and Wu, 1982; Pavlidis et al., 1994; Pavlidis and Tanouye, 1995; Kuebler and Tanouye, 2000). BS mutant stocks pick up modifiers which affect the penetrance of the alleles. For the strains reported on here, stocks were continuously selected for a robust and consistent paralytic phenotype.

The maleless (mle, 2-56.2) gene encodes an RNA helicase-like protein (Kernan et al., 1991; Lee and Hurwitz, 1993). The no-action potential temperature-sensitive allele (mle$^{napts}$) is a gain-of-function mutation that causes a reduction in adult brain voltage-gated Na$^+$ channels as assessed by tetrodotoxin-binding studies (Kauvar, 1982; Jackson et al., 1984). As described previously, mle$^{napts}$ mutants show a loss of action potentials and behavioral paralysis at elevated (37° C.) temperatures and increased action potential refractory period at room temperature (Wu et al., 1978; Wu and Ganetzky, 1980). In double mutant combinations, mle$^{napts}$ acts as a suppressor of BS and Sh behavioral phenotypes (Ganetzky and Wu, 1982); it causes unconditional lethality in combination with para (Wu and Gantezky, 1980).

The paralytic (para, 1-52.1) gene encodes a voltage-gated Na$^+$ channel alpha subunit (Loughney et al., 1989; Ramaswami and Tanouye, 1989). The para$^{ts1}$ allele causes a loss of action potentials and behavioral paralysis at elevated (29° C.) temperatures and increased action potential refractory period at room temperature (Suzuki et al., 1971; Siddiqi and Benzer, 1976; Wu and Ganetzky, 1980). The para$^{ST76}$ allele used here has been described previously (Siddiqi and Benzer, 1976) and appears to be less severe than para$^{ts1}$ based on viability in a mle$^{napts}$ background (Ganetzky, 1984).

The Shaker (Sh, 1-57.6) gene encodes several types of voltage-gated K$^+$ channel alpha subunits (Baumann et al., 1987; Kamb et al., 1987; Tempel et al., 1987). For mutants under moderate ether anesthesia, legs shake abnormally, antennae twitch, and abdomen pulsates. Mutations cause abnormal action potential repolarization of the adult giant fiber, repetitve firing of action potential in larval nerves, and prolonged transmitter release at the larval neuromuscular junction (Jan et al., 1977; Tanouye et al., 1981; Ganetzky and Wu, 1982; Tanouye and Ferrus, 1985). Mutants are abnormal in one class of K$^+$ current ($I_A$) (Salkoff and Wyman, 1981; Gautam and Tanouye, 1990; Lichtinghagen et al., 1990). The Sh$^{KS133}$ allele is an extreme mutation due to a single amino acid substitution that causes a non-functional channel subunit with a complete loss of $I_A$. The Sh5 allele is a less extreme mutation due to an amino acid substitution that changes $I_A$ channel kinetics. The Sh$^{tKO120}$ allele is the weakest mutation of the three and causes a slight decrease in $I_A$. In double mutant combinations, mle$^{napts}$ has been shown to suppress Sh behavioral phenotypes (Ganetzky and Wu, 1982).

The ether-a-go-go (eag, 1-50) gene encodes a cyclic nucleotide modulated K$^+$ channel (Warmke et al., 1991; Bruggemann et al., 1993). Similar to Sh, these mutants exhibit leg-shaking under ether and have abnormal K$^+$ currents in larval muscles (Wu et al., 1983). The eag1 mutation leads to the alteration but not the absence of four different K$^+$ currents in larval muscles (Zhong and Wu, 1991). In double mutant combination with Sh they show an enhancement of the Sh phenotype as described above (Ganetzky and Wu, 1983).

The slowpoke (slo, 3-86) gene encodes a Ca$^{2+}$ activated K$^+$ channel (Atkinson et al., 1991). The mutants exhibit temperature sensitive paralysis and are sluggish at room temperature (Elkins et al., 1986). The defect leads to a large reduction in the fast Ca$^{2+}$ activated K$^+$ current (ICF) in adults (Elkins et al., 1986) and larvae (Singh and Wu, 1989).

The shaking-B (shak-B, 1-64) gene encodes gap-junction proteins (Krishnan et al., 1993; Crompton et al., 1995; Phelan et al., 1998). The shak-B$^2$ allele prevents the formation of electrical synapses in the GF system, in the flight circuit, and likely in many other parts of the nervous system (Phelan et al., 1996; Trimarchi and Murphey, 1997). Mutations also display aberrant neuronal branching patterns and neuroconnectivity defects in the GF system ("Passover" defects, Thomas and Wyman, 1984). These lead to deficits in signalling (weak or no response) between the GF axon and the TTM motoneuron, and in the GF to DLM pathway. Behaviorally, mutants show no escape response: flies are unable to jump into the air and fly away at a light off stimulus.

The netrins encode secreted proteins that are involved in guiding the growth cone of axons. The netrin allele used, T9-B118 (Winberg et al., 1998) removes both the NetA and NetB transcription units, the only two netrin genes that have been found in Drosophila (Mitchell et al., 1996). Both genes map to the 12–13 region of the X chromosome. The deletion of both genes causes a reduction in the number of neurons that cross the midline in Drosophila embryos (Mitchell et al., 1996). The T9-B118 stock is female lethal but males are viable although they hold their wings perpendicular to the ground and are unable to fly.

To generate homozygous double mutants of the genotype bss;mle$^{napts}$, the first chromosome was tracked using the FM7a balancer chromosome and the second chromosome was tracked using the CyO balancer chromosome. The presence of mle$^{napts}$ in the homozygous double mutant stock was verified by the change in seizure threshold. The presence of bss in the stock was ascertained by back-crossing with bss; +/+ to generate flies of the genotype bss; mle$^{napts}$/+. These flies were not suppressed and resembled bss homozygous flies in phenotype. The bss; mle$^{napts}$/+ flies also served as control for non-specific genetic background effects and indicated that alterations in the seizure threshold were due to homozygous mle$^{napts}$ in the double mutant combination. Similar methods were used to construct and verify other double mutant combinations involving mutations on different chromosomes (mle$^{napts}$; sda, Sh$^{KS133}$; sda, shak-B$^2$;sda and para;sda).

To generate homozygous double mutants of the genotype eas shak-B$^2$, male recombinants were generated from heterozygous females of the genotype eas f/shak-B$^2$. The presence of shak-B$^2$ in the homozygous double mutant stock was verified by lack of response in the GF to DLM pathway. The presence of eas in the stock was ascertained by back-crossing with eas f to generate flies of the genotype eas shak-B$^2$/eas f. These flies resembled eas homozygous flies in phenotype as they had seizure thresholds similar to eas. They also served as control for non-specific genetic background effects as described, above. Similar methods were used to construct and verify bss shak-B$^2$.

Behavior and electrophysiology. Behavioral testing for bang-sensitive paralysis was performed by vortexing groups of 10 flies as described previously (Kuebler and Tanouye, 2000). In order to analyze better the bang-sensitive phenotypes of bss shak-B$^2$, eas shak-B$^2$, shak-B$^2$;sda, and Sh$^{KS133}$;sda double mutants, flies were vortexed individually.

The giant fiber (GF) circuit was used to assess nervous system function. Methods for handling and mounting flies, stimulating the GF with single pulses (0.2 msec duration, 0.5 Hz), and recording of evoked dorsal longitudinal muscle (DLM) potentials have been described previously (Pavlidis and Tanouye, 1995; Kuebler and Tanouye, 2000). Care was taken not to use flies from overcrowded vials, as the reduced size of these flies could artificially lower the seizure threshold.

To determine following frequency of the GF circuit, twenty consecutive supra-threshold stimulus pulses (1.2 to 1.4 times the GF threshold) were delivered to the GF at a particular frequency. The following frequency was determined as the highest frequency at which the DLM responded to at least nineteen of the twenty pulses. Between the different trials, flies were allowed to rest for at least one min. GF following frequencies were not determined for shak-B$^2$ because the GF pathway is disrupted in this mutant.

Seizures were elicited by short wavetrains of high frequency (HF) electrical stimuli delivered to the brain (0.5 msec pulses at 200 Hz for 300 msec). Methods for determining seizure thresholds and latency to seizure were as described (Kuebler and Tanouye, 2000). Some of the less susceptible genotypes examined here did not seize using 300 msec HF stimuli of our standard procedure. For these strains, a threshold could be determined following 400 msec HF stimuli as noted.

Previous experiments that examined seizure susceptibility were performed on female flies because they are larger in size (Pavlidis et al., 1994; Pavlidis and Tanouye, 1995; Kuebler and Tanouye, 2000). However, here we find that males have consistently lower seizure thresholds and have focused on them exclusively in order to facilitate our analysis of high threshold genotypes. As example, CS females have a seizure threshold of 44.5±4.4 V (Kuebler and Tanouye, 2000) while the male CS threshold is 30.1±3.8 V (Table 2). Likewise, OR males were found to have a lower threshold (39.3±6.6 V; Table 2) than females (48.4±3.6 V; Kuebler and Tanouye, 2000). Similar differences were observed in several of the mutant strains that we examined. For clarity here, only male thresholds are reported.

In addition to sex differences in seizure threshold, we also found males had lower GF thresholds than females. The threshold of this neuron, which is located in the brain, can be monitored with relative ease due to its synaptic connections to the large indirect flight muscles in the thorax. In all cases examined, the GF threshold in males (Table 2) was lower than that found previously in females (Kuebler and Tanouye, 2000).

Results. Seizure susceptibility differences in wild type strains. In order to compare the seizure susceptibility of different Drosophila strains it is important to control for various factors that may affect susceptibility. In many behaviors, learning and memory, ethanol resistance, etc., the genetic background of the fly can make a large contribution to the overall phenotype. We examined a variety of different wild type strains to assay the degree to which the genetic background affected seizure susceptibility. Berlin, CS and Oregon-R wild type strains had thresholds that ranged from 25 V to 40 V (Table 2). Based on these three strains, it appears that genetic background can modulate susceptibility over a fairly significant range. However, the majority of the mutants examined here have thresholds that are significantly removed from this range making most of our interpretations straightforward.

Seizure thresholds in $Na^+$ channel mutants. Previous studies have shown that the BS mutants are more susceptible to seizures than wild type (Kuebler and Tanouye, 2000). These mutants have seizure thresholds in the range of 3 V to 7 V (Table 2). Because of their phenotype, the BS mutants are a useful tool for investigating the types of genetic backgrounds that can suppress seizure susceptibility. To identify genetic backgrounds that may have this ability, we examined the seizure susceptibility of a variety of mutants that alter either neuronal excitability or neuronal connections. Mutants that displayed seizure thresholds that were elevated substantially compared to wild type were then tested in double mutant combination with specific BS mutants for the ability to suppress the BS seizure susceptible phenotype.

The first class of mutants we investigated consisted of two mutants that affect voltage-gated $Na^+$ channels, $mle^{napts}$ and para. These mutants seemed likely candidates for having alterations in seizure susceptibility as many anti-convulsants such as phenytoin, carbamazepine and lamotrigine suppress seizures through interactions with voltage-gated $Na^+$ channels (Kuo, 1998; Kuo et al., 1997). Both of these mutants displayed decreased levels of seizure susceptibility compared to wild type strains. The seizure threshold found for para was 65±7.2 V, well above the wild type range, while $mle^{napts}$ had no appreciable seizures following the standard 300 msec HF stimuli. With 400 msec stimuli, the seizure threshold for $mle^{napts}$ was 72±7.3 V.

Both $mle^{napts}$ and para suppress the BS seizure susceptible phenotype. Because both $mle^{napts}$ and para were much less susceptible to seizures than wild type, both mutants were tested for the ability to suppress BS seizures. The $mle^{napts}$ mutation was able to rescue the seizure susceptibility defect in the two BS mutants tested, bss and sda. The double mutant combination bss;$mle^{napts}$ has a seizure threshold of 29±4.7 V, which is in the range of wild type, as opposed to a 3.2±0.6 V threshold for bss. The $mle^{napts}$;sda double mutant had no appreciable seizures following 300 msec stimuli such that 400 msec stimuli had to be used. The value obtained, 89±10.2 V, is much greater than wild type values and is even slightly higher than that found for $mle^{napts}$ alone. The $mle^{napts}$ mutation also was able to suppress completely the BS behavioral phenotype in sda flies, a phenomenon previously demonstrated for the bss mutant (Gantezky and Wu, 1982). In addition to suppressing the BS behavioral and seizure phenotypes, the introduction of sda or bss into a $mle^{napts}$ background also led to a reduction in fertility. This was most evident in $mle^{napts}$;sda females which were unable to lay eggs.

The para mutation was also able to suppress the BS phenotype as the addition of sda into a para background raised the seizure threshold to wild type levels (38.9±8.0 V), well above the 6.2±0.8 V seizure threshold seen in the sda mutant. The para mutation also suppressed the behavioral bang-sensitivity normally seen in the sda mutant.

In both $mle^{napts}$ double mutants, bss;$mle^{napts}$ and $mle^{napts}$;sda, there was an absence of spontaneous activity upon recovery from seizure that may be related to the reduction in seizure susceptibility seen in these mutants. Following seizure and failure of the GF pathway in wild type and BS mutants, the flies display varying degrees of spontaneous activity. The BS flies always display intense spontaneous activity during this period, however, this activity was absent in both $mle^{napts}$ double mutants. Surprisingly, despite the change in seizure threshold, spontaneous activity was still present in the para;sda mutant and did not appear to be the least bit attenuated compared to sda.

Seizure thresholds in $K^+$ channel mutants. The second group of mutants examined consisted of Drosophila $K^+$ channel mutants. These mutants are likely candidates for having increased seizure susceptibility levels as $K^+$ channel defects can lead to seizure disorders in both mice and humans (Charlier et al., 1998; Singh et al., 1998; Smart et al., 1998). We tested three different mutant alleles of the Sh $K^+$ channel gene and surprisingly found that the Sh mutants were resistant to seizures in comparison to wild type strains. The most defective Sh mutant, $Sh^{KS133}$, was resistant to seizures following 300 msec HF stimuli and the seizure threshold, 84±12.8 V following 400 msec HF stimuli, was nearly the highest threshold seen in this study. Seizures seen in $Sh^{KS133}$ were often less robust than those seen in other genotypes although high-frequency seizures still did occur. The $Sh^{rKO120}$ mutant was also resistant to seizures compared to wild type as it was found to have a seizure threshold of at 87±8.5 V. The Sh5 mutant did not display much resistance to seizures; it has a seizure threshold of 51±6.1 V, a value just above the wild type range.

We also tested other $K^+$ channel mutants including eag, a member of a family of voltage-gated $K^+$ channels that is distantly related to the Sh family (Wu and Ganetzky, 1992). The eag mutant has a seizure phenotype similar to Sh as it has a seizure threshold above the wild type range (62±10.3 V). The final $K^+$ channel mutant tested was slo, a mutation that affects the calcium-activated $K^+$ current, ICF (Atkinson et al., 1991). The slo strain was also less susceptible to seizures in comparison to the wild type strains (52.9±7.4 V).

$Sh^{KS133}$ can partially suppress the BS seizure susceptible phenotype. The high seizure threshold in $Sh^{KS133}$ made this mutant a candidate for having the ability to suppress the BS seizure susceptible phenotype even though K$^+$ channels had not previously been thought of as targets for anticonvulsants. We found that the introduction of sda into a Sh$^{KS133}$ background led to partial suppression of the sda seizure susceptible phenotype. The Sh$^{KS133}$;sda double mutant has a seizure threshold (18.8±5.7 V) that is above the values for the BS mutants yet below the wild type range (Table 2).

The Sh$^{KS133}$ allele also suppressed the behavioral bang-sensitivity normally seen in sda mutants as none of the Sh$^{KS133}$;sda double mutants underwent paralysis following a mechanical vortex. However, roughly a quarter of the double mutant flies exhibited seizure-like convulsions immediately after the vortex. Unlike in the case of the BS mutants, the convulsions did not lead to paralysis as the presence of the Sh$^{KS133}$ allele appeared to suppress this. Consistent with this lack of paralysis, Sh$^{KS133}$;sda flies also exhibited a decrease in the GF failure time following HF stimuli. The double mutant failed for 25±7.4 sec while sda failed for 64±10.5 sec. The presence of Sh$^{KS133}$ appeared to suppress failure and paralysis and to a large extent seizures although the Sh$^{KS133}$;sda flies were still more susceptible than wild type.

Mutants that affect neural connections are resistant to seizures. The final class of mutants we investigated consisted of those that may affect neural connections. Two such mutants were studied, shak-B$^2$ and netrin. Because neural connections and pathways are thought to be critical in both the generation and spread of seizures throughout the nervous system, mutations that disrupt these connections may affect seizure susceptibility. In addition, the shak-B$^2$ mutant, which prevents the formation of electrical synapses throughout the nervous system (Phelan et al., 1996; Trimarchi and Murphey, 1997), may inhibit the synchronization of neuronal firing, a trademark of seizure activity (Perez-Velazquez et al., 1994; Carlen et al., 1996). Here we found that the shak-B$^2$ mutant has decreased susceptibility to seizures as the seizure threshold in this mutant, 95±10.2 V, is well above wild type levels. The netrin mutant, which is defective in a secreted axon guidance molecule, could lead to the absence or alteration of many synaptic connections. This mutant also has an elevated seizure threshold of 53±5.1 V, although, it is much closer to wild type than shak-B$^2$.

The shak-B$^2$ mutation suppresses different BS mutants to varying degrees. The shak-B$^2$ mutant was tested for its ability to suppress seizures in all three of the BS mutants studied here, bss, eas and sda. In the case of bss, the presence of the shak-B$^2$ mutation did not significantly alter the seizure susceptibility. There was little difference in the seizure thresholds between bss and bss shak-B$^2$ double mutants: bss shak-B mutants have a threshold of 3.6±0.7 V while bss mutants have a threshold of 3.2±0.6 V. The eas shak-B$^2$ double mutant displayed partial suppression as it has a seizure threshold (15.3±3.2 V) that falls between eas and the wild type range (Table 2). Finally, the addition of sda to a shak-B$^2$ background raised the seizure threshold to wild type levels (31.4±5.2 V), well above the 6.2±0.8 V seizure threshold seen in the sda mutant. The reduction in excitability in shakB;sda mutants was also evident by the absence of spontaneous activity upon recovery from seizure described previously for bss;mle$^{napts}$ and mle$^{napts}$;sda.

A similar pattern was seen upon examining behavioral bang-sensitivity in these mutants. The presence of the shak-B$^2$ mutation was most effective at suppressing the BS behavioral phenotype in sda as 100% of shak-B$^2$;sda flies were resistant to seizure and paralysis following mechanical shock. It was less effective at suppressing eas as 85% of the eas shak-B$^2$ mutants were resistant and it was least effective with bss as only 58% of the bss shak-B$^2$ double mutants were resistant to mechanical shock. In all three cases, a population of flies, which did not undergo seizure and paralysis, exhibited uncoordinated hyperactivity immediately following the mechanical vortex during the time the flies tried to right themselves. This behavior, which lasted from 1–5 seconds, was quite different from the characteristic bang-sensitive response and occurred in approximately 30% of the bss shak-B$^2$ and eas shak-B$^2$ flies and in less than 20% of shak-B$^2$;sda flies. A similar behavior was seen in rare instances in shakB flies following a vortex.

Increased latency to seizures and reduction of spontaneous seizures in bss shak-B$^2$. Despite the lack of ability to alter the seizure threshold in bss flies, the presence of the shak-B$^2$ mutation led to a significant increase in the latency to seizure onset in bss shak-B$^2$ flies following 4 V HF stimuli. In the case of the double mutant, the latency to seizure onset was 768±371 msec, while the latency for bss was 295±81 msec (n=20). Previous studies (Kuebler and Tanouye, 2000) have shown that in bss, low voltage HF stimuli give rise to seizures with longer latencies possibly because it takes some time for the activity in the few neurons activated by the HF stimulus to be amplified through positive feedback loops to generate a seizure. When higher voltage HF stimuli are used, more neurons are recruited directly by the stimulus and therefore less time is taken for this activity to be amplified into a seizure. The absence of functional electrical connections in bss shak-B$^2$ flies may increase the amount of time necessary to generate a seizure by disrupting the amplification of the neural activity induced by the HF stimuli.

A reduction in excitability in the bss shak-B$^2$ mutant could also be seen upon examining the level of spontaneous activity seen upon recovery from synaptic failure. Following electrically induced seizure and synaptic failure, bss mutants often undergo spontaneous activity that resembles the initial seizure. These spontaneous seizures differ from normal spontaneous activity in that they are followed by GF failure and another bout of spontaneous activity before recovery of the pathway. Spontaneous seizures occurred in 87% of bss flies during recovery from a 4 V HF stimulus, while spontaneous seizures only occurred in 12% of the bss shak-B$^2$ mutants. The absence of the electrical connections may disrupt the amplification or synchronization of the spontaneous activity that occurs following synaptic failure such that it is much more difficult to generate spontaneous seizures in these double mutants.

Double mutants: general features. Our general findings are that although all of the BS mutations examined could be suppressed in double mutant combinations, they did not all appear to be suppressed equally well. The bss mutant was the most difficult to suppress, sda appeared to be the easiest to. suppress, while eas was somewhere in between. In addition, the mutations that we used to set the genetic background had varying abilities to act as suppressors. For the mutants tested, mle$^{napts}$ acted as the best suppressor, Sh$^{KS133}$ appeared to be the weakest of the suppressors, while the para and shak-B$^2$ mutations fell somewhere in between.

The double mutant combinations displayed seizure thresholds that spanned an extremely large range. Despite this large range, most of the double mutants fell into three broad categories. The first consisted of those with a partially suppressed BS seizure susceptibility phenotype and included eas shak-B$^2$ and Sh$^{KS133}$;sda. These flies had seizure thresholds that were above the BS level but below wild type and only a small percentage (if any) displayed behavioral bang-sensitivity. The second category consisted of those with a completely suppressed BS phenotype and included bss;mle$^{napts}$, shak-B$^2$;sda and para;sda. These flies had seizure thresholds that were similar to wild type and did not display any behavioral bang-sensitivity. The final category consisted of those that were less susceptible to seizures than wild type. This category had only one representative, mle$^{napts}$;sda, a double mutant that was also the most unhealthy of all the combinations generated. Only one double mutant did not fall into one of these categories, bss shak-B$^2$. These flies did not display any change in the seizure threshold as compared to the BS mutants, although the behavioral phenotype, partial suppression of bang-sensitivity, did correspond to the first category of double mutants.

The GF threshold is not altered in most strains. One possible explanation for the altered seizure thresholds seen in many of the double mutants is that the threshold of each individual neuron in these strains could be altered. If this were the case, different HF stimulus voltages could be required to recruit the same number of neurons in different genotypes. This would account for the different seizure threshold seen here. In order to investigate this possibility we examined the threshold of the giant fiber (GF) neuron to determine if individual neuron thresholds were significantly altered in these strains. We found that the GF threshold was not altered in the majority of cases (Table 2). Only two double mutants, mle$^{napts}$;sda; and bss;mle$^{napts}$, have GF thresholds significantly different from wild type strains. In both cases, the GF threshold is elevated, a factor which may contribute to the fact that mle$^{napts}$ is the best suppressor we have studied. The GE threshold did not necessarily correlate with the seizure threshold in these cases: the double mutant bss;mle$^{napts}$ has a higher GF threshold than mle$^{napts}$ alone despite the fact that the double mutant has a much lower seizure threshold. Elevations in the GF threshold in the two double mutants also may contribute to the unhealthy state of these two stocks.

The only other strain that has a GF threshold significantly different from wild type is mle$^{napts}$. In the case of mle$^{napts}$, another neuron, the DLM motoneuron, showed no changes in the stimulation threshold (Kuebler and Tanouye, 2000). These data indicate that individual neuron thresholds do not account for the alterations in seizure susceptibility.

Following frequency alterations. The response of the GF pathway to single pulse stimulation in these strains revealed that, in most cases, individual neuron thresholds are not altered despite the changes in seizure threshold. Another method for examining the excitability of the nervous system in the various strains is to determine the GF following frequency, the maximum stimulation frequency the GF pathway can reliably follow. This could be more relevant to seizure susceptibility as it may be indicative of the nervous systems ability to support the high frequency activity that is characteristic of seizures. We have found significant differences between genotypes in GF following high frequency, and we believe this may be one factor that contributes to seizure susceptibility.

The first indication that GF following frequency may affect the seizure threshold is seen upon examining the mutants with the highest thresholds, Sh$^{KS133}$ and mle$^{napts}$. These mutants do not display seizures following 300 msec HF stimuli and both have following frequencies that are well below the wild type range (Table 3). Likewise, the Sh$^{tKO120}$ and para mutants, which have seizure thresholds that fall between wild type and the high threshold mutants, have GF following frequencies that were intermediate between these two groups.

Further evidence is seen in the fact that all the double mutant combinations that show a decrease in seizure susceptibility also display a decrease in the GF following frequency. The bss; mle$^{napts}$ and mle$^{napts}$;sda double mutants have GF following frequencies that are greatly reduced compared to the following frequencies seen in bss and sda respectively (Table 3). In both cases the following frequency was reduced to levels similar to mle$^{napts}$. In the case of para;sda, the double mutant has a following frequency that is lower than either sda or para alone. Finally, the addition of sda to a Sh$^{KS133}$ background reduced the following frequency well below the value found for sda. In all cases, the reduction in GF following frequency corresponded to a complete or partial suppression of the seizure susceptible phenotype normally seen in the BS mutants.

Despite these correlations, GF following frequency was not an absolute predictor of seizure susceptibility. For example, para;sda has a lower following frequency than mle$^{napts}$;sda despite having a higher level of seizure susceptibility. In fact, a low following frequency did not always correspond with a high seizure threshold indicating that other factors are involved. The Sk$^{KS133}$;sda double mutant is a case in point as it has one of the lowest following frequencies yet has a seizure threshold that is below wild type. If the reduction in following frequency does indeed have an anti-convulsant effect, this effect may be partially compensated for in Sh$^{KS133}$;sda mutants by other hyperexcitable defects associated with the Sh$^{KS133}$ or sda mutations.

We also tested the GF following frequency of the BS mutants and found that bss, eas, sda had following frequencies similar to wild type. It is clear that the seizure susceptibility seen in these mutants is not due to increased following frequencies indicating other mechanisms must account for the phenotype seen in the BS mutants. In addition, the following frequencies of two BS mutants, bss and eas, are slightly but significantly lower than CS wild type flies, despite the lower seizure threshold in these mutants. It is clear that the following frequency does not always predict the seizure susceptibility level, however, it appears that modifications in following frequency are one factor that contributes to the overall seizure susceptibility of the nervous system.

This Example demonstrates that genetic mutations can both elevate the seizure threshold in Drosophila and suppress the seizure susceptible phenotype seen in BS mutants. All of these mutants provided a genetic background that elevated the seizure threshold to values above those seen in BS mutants alone. This is the first demonstration that mutations in Na$^+$ channels, K$^+$ channels and a connexin protein can suppress seizures.

REFERENCES

Atkinson N S, et al. (1991) Science 253:551–555.
Baumann A, et al. (1987) EMBO J 6:3419–3429.
Benzer S (1971) J Am Med Assoc 218:1015–1022.
Biervert C, et al. (1998) Science 279:403–406.
Bruggemann A, et al. (1993) Nature 365:445–448.
Carlen P L,et al. :(1996) Gap junctions in the nervous system. (Spray D C, Dermietzel R, eds), pp 289–299. New York: RG Landes.
Charlier C, et al. (1998) Nat Gen 18:53–55.
Crompton D, et al (1995) Dev Biol 170:142–158.
Durner M, et al. (1991) Neurology 41:1651–1655.
Elkins T, et al. (1986) Proc Natl Acad Sci USA 83:8415–8419.
Ganetzky B (1984) Genetics 108:897–911.
Ganetzky B, et al. (1983) J Neurogen 1:17–28.

Gautam M, et al. (1990) Neuron 5:67–73.
Jackson F R, et al. (1984) Nature 308:189–191.
Jan Y N, et al (1977) Proc R Soc Lond 198:87–108.
Kamb A, et al. (1987) Cell 50:405–413.
Kamb A, et al. (1988) Neuron 1:421–430.
Kauvar L M (1982) Gen Genet 187:172–173.
Kokaia M, et al. (1995) Exp Neurol 133:215–224.
Krishnan et al. (I1993) Cell 73:967–977.
Kuebler D, et al. (2000) J Neurophysiol 83:998–1009.
Kuo C C (1998) Mol Pharmacol 54:712–721.
Kuo C C, et al. (1997) Mol Pharmacol 51:1077–83.
Lichtinghagen R, et al (1990) EMBO J 9:4399–4407.
Loughney K, et al. (1989) Cell 58:1143–1154.
McNamara J O (1999) Nature (Sup) 399:A15–A22
Mitchell K J, et al. (1996) Neuron 17:203–215.
Perez-Velazquez J L, et al. (1994) J Neurosci 14:4308–4317
Phelan P, et al. (1996) J Neurosci 16:1101–1113
Phelan P, et al. (1998) Nature 391:181–184
Puranam R S, McNamara J O (1999) Curr Opin Neurobiol 9:281–287
Ramaswami M,. Tanouye M A (1989) Proc Natl Acad Sci USA 86:2079–2082
Salkoff L, Wyman R (1981) Nature 293:228–230
Siddiqi O, Benzer S (1976) Proc Natl Acad Sci USA 73:3253–3257
Singh N A, et al. (1998). Nat Gen 18:25–29
Singh S, Wu CF (1989) Neuron 2:1325–1329
Suzuki D, et al. (1971) Proc Natl Acad Sci USA 68:890–893
Tanouye M A, Ferrus A (1985) J Neurogen 2:253–271.
Tanouye M A, et al. (1981) Proc Natl Acad Sci USA 78:6548–6552.
Tempel B L, et al. (1987) Science 237:770–775.
Thomas J B, et al. (1984) J Neurosci 4:530–538.
Trimarchi J R, et al. (1997). J Neurosci 17:4700–4710.
Warmke J, et al. (1991) Science 252:1560–1562.
Watanabe Y, et al. (1996) J Neurosci 16:3827–3836.
Winberg M L, et al. (1998) Cell 93:581–591.
Wu C F, Ganetzky B (1980) Nature 286:814–816.
Wu C F, Ganetzky B (1992) Neurogenetic studies of ion channels in Drosophila. In: Ion channels Volume 3 (Narahashi T, ed), pp 261–314. New York: Plenum Press.
Wu C F, et al. (1. 978) Proc Natl Acad Sci USA 75:4047–4051.
Wu C F, et al (1983) Science 220:1076–1078.
Zhong Y, et al. (1991) Science 252:1562–1564.

TABLE 2

Threshold values for various genotypes tested. Values for the GF stimulation threshold and the seizure threshold are listed for each genotype that was tested. $Sh^{KS133}$, $mle^{napts}$ and $sda;mle^{napts}$ mutants displayed no seizures following 300 msec HF stimuli. Thresholds for these mutants were determined following 400 msec HF stimuli and are marked by an asterisk. GF thresholds were not obtained for $shak-B^2$ mutants as they are defective in this pathway. Values listed are means ± standard deviation. (n > 13 for each genotype tested.)

| Genotype | GF Threshold | Seizure Threshold |
|---|---|---|
| bss | 1.6 ± 0.37 | 3.2 ± 0.6 |
| eas | 1.7 ± 0.34 | 3.4 ± 0.5 |
| bss shak-$B^2$ | — | 3.6 ± 0.7 |
| sda | 1.6 ± 0.37 | 6.2 ± 0.8 |
| eas shak-$B^2$ | — | 15.3 ± 3.2 |
| $Sh^{KS133}$;sda | 1.7 ± 0.33 | 18.8 ± 5.7 |
| Berlin | 1.7 ± 0.37 | 25.5 ± 3.7 |
| bss; $mle^{napts}$ | 4.0 ± 0.82 | 29.2 ± 4.7 |
| CS | 1.6 ± 0.39 | 30.1 ± 3.8 |
| shak-$B^2$;sda | — | 31.4 ± 5.2 |
| para;sda | 1.7 ± 0.38 | 38.9 ± 8.0 |

TABLE 2-continued

Threshold values for various genotypes tested. Values for the GF stimulation threshold and the seizure threshold are listed for each genotype that was tested. $Sh^{KS133}$, $mle^{napts}$ and $sda;mle^{napts}$ mutants displayed no seizures following 300 msec HF stimuli. Thresholds for these mutants were determined following 400 msec HF stimuli and are marked by an asterisk. GF thresholds were not obtained for $shak-B^2$ mutants as they are defective in this pathway. Values listed are means ± standard deviation. (n > 13 for each genotype tested.)

| Genotype | GF Threshold | Seizure Threshold |
|---|---|---|
| Oregon-R | 1.8 ± 0.34 | 39.3 ± 6.6 |
| Sh5 | 1.5 ± 0.27 | 51.3 ± 6.1 |
| slo | 1.7 ± 0.34 | 52.9 ± 7.4 |
| netrin | 1.7 ± 0.42 | 53.4 ± 5.1 |
| eag | 1.5 ± 0.29 | 62.1 ± 10.3 |
| para | 1.9 ± 0.37 | 65.0 ± 7.2 |
| $Sh^{rko120}$ | 1.7 ± 0.42 | 86.9 ± 8.5 |
| shak-$B^2$ | — | 94.7 ± 10.2 |
| $mle^{napts*}$ | 2.5 ± 0.50 | 72.2 ± 7.3 |
| $Sh^{KS133*}$ | 1.8 ± 0.25 | 83.8 ± 12.8 |
| $mle^{napts}$;sda* | 4.7 ± 1.12 | 88.8 ± 10.2 |

TABLE 3

GF following frequencies for the various genotypes tested. Values for the GF following frequency are listed for each genotype that was tested. Values listed are means ± standard deviation. (n > 9 for each genotype tested.)

| Genotype | GF Following Frequency | Genotype | GF Following Frequency |
|---|---|---|---|
| CS | 137 ± 14.7 | $Sh^{rko120}$ | 72.1 ± 16.9 |
| Berlin | 133 ± 10.2 | $Sh^5$ | 68.4 ± 15.8 |
| sda | 131 ± 17.6 | $mle^{napts}$ | 59.4 ± 14.1 |
| eag | 116 ± 14.7 | bss $mle^{napts}$ | 59.3 ± 16.4 |
| bss | 102 ± 17.1 | $mle^{napts}$; sda | 51.0 ± 18.2 |
| eas | 103 ± 16.0 | $Sh^{KS133}$; sda | 37.1 ± 12.0 |
| Oregon-R | 98 ± 16.5 | $Sh^{KS133}$ | 35.2 ± 13.8 |
| para | 88.2 ± 10.3 | para;sda | 36.2 ± 20.0 |

III. Anti-convulsant Assays in Epileptic (EL) Mouse Model

Inbred EL/Suz (EL) mice and the nonepileptic DDY mice are obtained from The Jackson Laboratory, Bar Harbor, Me., U.S.A. The inbred nonepileptic ABP/LeJ (ABP) strain is also purchased from the Jackson Laboratory. Mice are housed in plastic cages with Sani-chip bedding that is changed once per week. The mice are kept on a 12-h light/dark cycle with food (Agway Prolab Rat, Mouse, Hamster 3000) and water provided ad libitum. The procedures used for all mice are in strict accordance with the NIH *Guide for the Care and Use of Laboratory Animals* and are approved by the Institutional Animal Care Committee.

EL and ABP mice are crossed to produce reciprocal $F_1$ hybrids. The female mouse is presented first in a corss (e.g., the ABP×EL $F_1$ hybrid is derived from crossing an ABP female with an EL male). A total of 582 mice are analyzed in this study.

Seizure test: A recently developed (Todorova, M. T. et al., 1999, Epilepsia, Vol. 40, No. 12, pp. 1697–1707) seizure-testing procedure is used that involves repetitive handling and stimulates the situation normally associated with routine cage changing (e.g., picking the mouse up by the tail for short intervals and moving it from a home cage to a new cage with fresh bedding). The test includes two phases (I and II) that are separated by 1 week. Each phase involves two handling trials (A and B) that are separated by 30 min. In each trial, a mouse is held by the tail for 30 s~10–15 cm above the bedding of its home cage. The mouse is then placed in a cage containing fresh bedding for 2 min. The mouse is held again for 15 s and then returned to the home cage. The test is repeated after 1 week (phase II). Mice are undisturbed (no cage changing) for 1 week before testing, and all tests are performed between 1 and 6 p.m.

Seizure phenotype: Mice are characterized as seizure susceptible if they experience a generalized seizure. This involves loss of postural equilibrium and consciousness, together with excessive salivation, head, limb, and chewing/swallowing automatisms. An erect forward-arching Straub tail, indicative of spinal cord activation, also is observed in most mice having generalized seizure. Mice that express vocalization or twitching, which does not progress to generalized seizure, are not considered seizure susceptible.

Statistical analysis: The $\chi^2$ test with a 2×2 contingency table is used to evaluate the significance of environmental influences on seizure susceptibility. The Mann-Whitney U test is used only to evaluate differences in the number of seizures per test per mouse. Candidate suppressors are shown to provide significant reduction in seizure phenotype.

IV. Convulsive Assays in Intracerebroventricular (i.c.v.) Administered Rat Model Intracerebroventricular (i.c.v.) administration to rats. Male Sprague-Dawley rats are anesthetized with sodim pentobarbital (40 mg/kg i.p., Entobar®, Hanlim Pharmaceutical, Seoul, Korea) and then mounted in a stereotaxic frame (David Kopf Instruments, Model 900). The surface of the skull is exposed and the head is oriented such that the skull sutures bregma and lambda are at the same vertical levels. A burr hole is drilled through the skull over a desired location (from bregma: 0.5 mm posterior, 1.3 mm left). For chronic i.c.v. cannulation, a stainless steel guide cannula (26 gauge) is implanted to terminate 1 mm above the left lateral ventricle (4 mm ventral from the skull surface). This cannula is secured to the skull with three stainless steel machine screws and dental acrylic and then plugged with a stylet (32 gauge). Animals are allowed 7–8 days to recover. During the recovery period before the actual experiment, animals are acclimated to handling such as mock i.c.v. injections and to a Plexiglas experimental cage (10" long×3.5" wide×3" deep). At the time of the experiment, animals are placed in experimental cages. When animals are resting quietly, a 33-gauge stainless steel injector is lowered into the lateral ventricle through the guide cannula after removing the stylet. The length of the injector is measured precisely to extend 1 mm beyond the tip of the guide cannula. Saline vehicle or graded doses (25–3000 mmol/rat) of β-lactam antibiotics (positive controls) or test anti-convulsant agent dissolved in 0.9% saline are administered into the lateral ventricle in a volume of 5 µl over 30 s through the injector conected to a 10-µl Hamilton syringe by PE-10 tubing. Drug delivery is confirmed by the movement of a small air bubble introduced into the PE-10 tubing. The injector is allowed to remain in place for a total of 5 min following the initiation of drug injection. The rats are observed for the presence of convulsions for 2 h after i.c.v. administration. The protocol was adapted from Jin, C. et al. (1999) Toxicology Vol. 138 pp.59–67. Candidate inducers are shown to provide significant increase in seizure phenotype.

V. Convulsive Activity Assay in the Mouse PTZ Convulsive Model

Groups of~10–50 male ICR mice are given 0.9% saline or a test anti-convulsant agent (200–800 mg/kg) dissolved in saline by i.v. bolus injection into the tail vein (0.01 ml/g). After 5 min, graded doses (40–60 mg/kg) of PTZ are injected by the intraperitoneal route. Mice are observed for the presence of tonic or tonic-extensor convulsions for 60 min after the injection of PTZ. The number of mice showing convulsions in each group is recorded. See, Jin, C. et al. (1999) Toxicology Vol. 138 pp.59–67. Candidate suppressors are shown to provide significant reduction in seizure phenotype.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inducing seizure in a fly, comprising the steps of:

electrically stimulating a fly which has not been subject to anesthesia; and detecting resultant seizure induction in the fly.

2. A method according to claim 1, wherein the fly is immobilized by mechanics, adhesive or vacuum.

3. A method according to claim 1, wherein the fly is stimulated with an electrode tip having a diameter less than 20 um.

4. A method according to claim 1, wherein the fly is stimulated with an electrode tip having a diameter less than 5 um.

5. A method according to claim 1, wherein the fly is a bang-sensitive mutant and the electrically stimulating step is effected with less than 20V.

6. A method according to claim 1, wherein the fly is a wild-type fly and the electrically stimulating step is effected with 25–40V.

7. A method according to claim 1, wherein the fly is one of a population of flies which have not been subject to anesthesia, the method further comprises electrically stimulating each of the flies and detecting resultant seizure induction in most of the flies.

8. A method according to claim 1, wherein the fly is a Drosophila.

9. A method for inducing seizure in a fly, comprising the steps of:

electrically stimulating a bang-sensitive fly with less than 20V; and detecting resultant seizure induction in the fly.

10. A method according to claim 9, wherein the electrically stimulating step is effected with less than 10V.

11. A method according to claim 9, wherein the fly is immobilized by mechanics, adhesive or vacuum.

12. A method according to claim 9, wherein the fly is stimulated with an electrode tip having a diameter less than 20 um.

13. A method according to claim 9, wherein the fly is stimulated with an electrode tip having a diameter less than 5 um.

14. A method for inducing seizure in a fly, comprising the steps of:

electrically stimulating a non-bang-sensitive fly with 25–40V; and detecting resultant seizure induction in the fly.

15. A method according to claim 14, wherein the fly is immobilized by mechanics, adhesive or vacuum.

16. A method according to claim 14, wherein the fly is stimulated with an electrode tip having a diameter less than 20 um.

17. A method according to claim 14, wherein the fly is stimulated with an electrode tip having a diameter less than 5 um.

18. A method for inducing seizure in wild-type flies, comprising the steps of:

electrically stimulating a population of non-bang-sensitive flies; and detecting resultant seizure induction in most of the flies.

19. A method according to claim 18, wherein the flies are immobilized by mechanics, adhesive or vacuum.

20. A method according to claim 18, wherein the flies are stimulated with an electrode tip having a diameter less than 20 um.

21. A method according to claim 18, wherein the flies are stimulated with an electrode tip having a diameter less than 5 um.

22. A method according to claim 18, wherein the non-bang-sensitive fly is a wild-type Drosophila.

* * * * *